United States Patent
Fell et al.

(10) Patent No.: US 6,504,043 B2
(45) Date of Patent: Jan. 7, 2003

(54) COLOR-STABLE SOLUTION OF DIMETHYLAMINOACETONITRILE IN WATER AND PROCESS FOR PREPARING IT

(75) Inventors: Rainer Fell, Langweid; Götz Wilbert, Gersthofen; Thomas Stährfeldt, Weil am Rhein, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/799,389

(22) Filed: Mar. 5, 2001

(65) Prior Publication Data

US 2002/0058830 A1 May 16, 2002

(30) Foreign Application Priority Data

Mar. 3, 2000 (DE) .......................... 100 10 593

(51) Int. Cl.⁷ ............................. C07C 255/24
(52) U.S. Cl. ................. 558/315; 558/303; 558/308
(58) Field of Search ................. 558/303, 315, 558/308

(56) References Cited

U.S. PATENT DOCUMENTS

| | | | | |
|---|---|---|---|---|
| 4,011,254 A | * | 3/1977 | Kobayashi et al. | 260/465.5 |
| 4,022,815 A | * | 5/1977 | Schlecht et al. | 558/315 |
| 4,113,764 A | | 9/1978 | Distler et al. | |
| 4,176,133 A | * | 11/1979 | Lenthe et al. | 260/465.5 |

FOREIGN PATENT DOCUMENTS

| | | |
|---|---|---|
| DE | 25 03 582 | 8/1976 |
| DE | 25 55 769 | 6/1977 |
| DE | 27 42 911 | 5/1978 |
| DE | 2840990 * | 9/1978 |
| DE | 27 48 964 | 5/1979 |
| FR | 95 268 | 8/1970 |
| GB | 1176581 | 1/1970 |
| GB | 1 467 751 | 3/1977 |

OTHER PUBLICATIONS

English abstract for DE 2742911, May, 11, 1978.
English abstract for JP 54–046720, Apr. 12, 1979.
W. Eschweiler, Justus Liebig's Annalen Der Chemie, 1894, 279, pp. 39–44.
R.A. Turner, "β–Dimethylaminoethylamine and Dimethylaminoacetonitrile", J. Am. Chem. Soc., 1946, 68, 1607–1608.

* cited by examiner

Primary Examiner—Floyd D. Higel
Assistant Examiner—Kamal Saeed
(74) Attorney, Agent, or Firm—Anthony A. Bisulca

(57) ABSTRACT

The present invention relates to a process for preparing a colour-stable, aqueous dimethylaminoacetonitrile solution from a formaldehyde source, dimethylamine and hydrocyanic acid, wherein the reaction mixture contains 2,4-diamino-6-phenyl-1,3,5-triazine(benzoguanamine) in a concentration of from 0.001 to 5% by weight, based on formaldehyde, prior to the reaction and the starting substances are used stoichiometrically or in a ratio of 0.98–1.02 mol of formaldehyde and 0.95–1.10 mol of dimethylamine per mol of hydrocyanic acid. The resulting product remains colour-stable without a further purification step even after prolonged storage.

15 Claims, No Drawings

COLOR-STABLE SOLUTION OF DIMETHYLAMINOACETONITRILE IN WATER AND PROCESS FOR PREPARING IT

FIELD OF THE INVENTION

The present invention relates to a colour-stable solution of dimethylaminoacetonitrile in water and to a process for preparing it.

BACKGROUND OF THE INVENTION

Aminoacetonitriles have been known for many decades (W. Eschweiler, Annalen 1894, 279, 34–44). The industrial production of representatives of this class of compounds is described in, for example, DE-A-2503582. These compounds are valuable starting materials for various fine chemicals. For example, various derivatives of glycine can be produced from these products. Thus, the potassium salt of N,N-dimethylglycine can be obtained from N,N-dimethylaminoacetonitrile by saponification with KOH (DE-A-2503582). Reaction of N,N-dimethylaminoacetonitrile with chlorine gives tetrachloroethylene bisisocyanide dichloride, a starting compound for the fungicide 2-methylimino-3-(4'-chlorophenyl)-4,5-bis (trifluoromethylimino) (DE-A2748964). N,N-Dimethylaminoacetonitrile is also a synthetic building block for α-sinensal, a sesquiterpene aldehyde used as a flavour (GB-A-1467751).

Dimethylaminoacetonitrile (hereinafter referred to as DMAA) is prepared using the amine and liquid hydrocyanic acid together with a formaldehyde source (formalin, paraformaldehyde). The usual procedure is to combine an aqueous formaldehyde solution slowly with liquid hydrocyanic acid and an aqueous dimethylamine solution [$1^{st}$ step of the Strecker amino acid synthesis (H. Beyer, Lehrbuch der Organischen Chemie, $23^{rd}$ edition, Hirzel Verlag, Stuttgart, 1998, p. 302)]. The reaction can be carried out in a stirred vessel or alternatively in a continuously operated mixing apparatus.

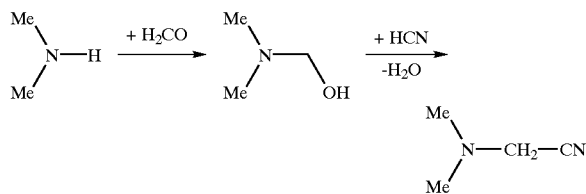

The reaction of paraformaldehyde with liquid hydrocyanic acid and an aqueous dimethylamine solution also leads to the desired end product. It should be noted here that the use of a solid (paraformaldehyde) in industry usually leads to undesirable and costly additional complication, which is accepted in the synthesis of glycine (Ullmanns Encyclopädie der technischen Chemie, Volume 7, $4^{th}$ edition, 1974, VCH, Weinheim, p. 432).

An aqueous solution of DMAA is obtained after the reaction. Further chemicals which may be present in the end product, usually in low concentration, are the amine used, residual formalin, HCN, the intermediate dimethylaminomethanol, bis(dimethylamino)methane and various stabilizers. The stabilizers are, for example, substances by means of which the aqueous formaldehyde solution is stabilized. In many cases, the purity of the DMAA solution is of critical importance. Thus, the concentrations should be as low as possible, in particular as regards the starting materials and by-products which are harmful to health.

It may also be found that the quality of the DMAA solution deteriorates on storage. Here, the colour of the solution in particular is a feature which worsens during storage. For this reason, usual industrial practice is to process the DMAA solution further immediately or to distil it before storage. The former is often not possible for logistical reasons and the latter is cumbersome and makes the DMAA solution significantly more expensive.

SUMMARY OF THE INVENTION

There is therefore a need for an inexpensive process in which a very pure DMAA solution is obtained directly in a storage-stable form.

DESCRIPTION OF THE PREFERRED EMBODIMENTS

It has surprisingly been found that a colour-stable aqueous solution of DMAA is obtained when the aqueous formaldehyde solution is stabilized with 2,4-diamino-6-phenyl-1,3,5-triazine(benzoguanamine).

An aqueous formaldehyde solution is customarily stabilized by means of an alcohol—usually methanol. However, if the formaldehyde solution is stabilized with benzoguanamine, gentle reaction of this solution with dimethylamine (preferably in aqueous solution) and liquid hydrocyanic acid gives a DMAA solution which is very pure and storage-stable without further work-up. A DMAA solution prepared according to the invention has a storage stability equivalent to that of a distilled DMAA solution and is considerably superior, particularly in respect of colour stability, to a conventionally prepared solution.

The stabilizer benzoguanamine is particularly advantageously used in a concentration of from 0.05 to 0.7% by weight, based on formaldehyde.

A suitable DMAA solution is obtained when the dimethylamine is reacted with liquid hydrocyanic acid and a formaldehyde source (formalin or paraformaldehyde) in the presence of 2,4-diamino-6-phenyl-1,3,5-triazine and water for from 5 minutes to 5 hours at a temperature of from 0 to 50° C. If the formaldehyde source is initially charged and, after addition of the aqueous amine solution a little at a time, dimethylaminomethanol is prepared as an intermediate, the liquid hydrocyanic acid can subsequently be added quite rapidly. However, the temperature should not exceed 500° C. in either step; both steps are particularly advantageously carried out at from 25 to 350° C. The reaction is also suitable for a continuously operated process. Here too, the reaction temperature should remain below 50° C.

The starting substances can be used in a stoichiometric amount or in a slight excess; preference is given to using 0.98–1.02 mol of formaldehyde and 0.95–1.10 mol of dimethylamine per mol of hydrocyanic acid.

The invention thus provides a process for preparing an aqueous DMAA solution from a formaldehyde source, in particular an aqueous formaldehyde solution, dimethylamine and hydrocyanic acid, wherein the reaction mixture contains 2,4-diamino-6-phenyl-1,3,5-triazine (benzoguanamine) in a concentration of from 0.001 to 5% by weight, based on formaldehyde, prior to the reaction and the starting substances are used stoichiometrically or in a ratio of 0.98–1.02 mol of formaldehyde and 0.95–1.10 mol of dimethylamine per mol of hydrocyanic acid.

As formaldehyde source, it is possible to use paraformaldehyde or formaldehyde in gaseous or liquid form or formaldehyde as an aqueous solution. In the latter case, a formaldehyde concentration of from 20 to 50% by weight in water is advantageous; an aqueous solution having a formaldehyde content of from 30 to 40% by weight is particularly useful. The dimethylamine can be used in liquid or gaseous form or advantageously in aqueous solution. In the latter case, the dimethylamine is present in the aqueous solution in a concentration of from 20 to 80% by weight, particularly advantageously from 35 to 65% by weight.

The surprising action of the stabilizer used according to the invention is restricted to an aqueous DMAA solution, since few other amines form water-soluble aminoacetonitriles.

It could be assumed that the unsatisfactory storage stability of the conventional DMAA solution is attributable to the presence of methanol as formalin stabilizer. The presence of methanol can be avoided by the alternative use of paraformaldehyde. This alternative is associated with the problems of solids processing and correspondingly higher costs, which is undesirable. Although a quite clean DMAA solution prepared using paraformaldehyde has a very good colour (which is fully comparable with that of a distilled solution) immediately after the synthesis, it likewise tends to become distinctly darker during storage.

It can thus be stated that a 2,4-diamino-6-phenyl-1,3,5-triazine-containing DMAA solution is significantly more colour stable than a 2,4-diamino-6-phenyl-1,3,5-triazine-free solution prepared using paraformaldehyde. Only when the DMAA solution has been subjected to costly distillation (in which 47% of DMAA together with 53% of water go over as an azeotrope; R. A. Turner, J. Am. Chem. Soc. 1946, 68, 1607–1608), can the presence of 2,4-diamino-6-phenyl-1,3,5-triazine be dispensed with. The synthesis in the presence of 2,4-diamino-6-phenyl-1,3,5-triazine thus gives a colour stability which is similar to that which can be achieved by distillation, but saves this additional and costly process step.

The invention therefore also provides a DMAA solution containing 2,4-diamino-6-phenyl-1,3,5-triazine. The concentration of 2,4-diamino-6-phenyl-1,3,5-triazine in the DMAA solution is from 0.001 to 2.0% by weight, based on the DMAA, preferably from 0.01 to 0.25% by weight.

The following examples illustrate the invention. The percentages quoted are by weight.

EXAMPLES

Comparative Example 1

Preparation of an Aqueous DMAA Solution from Methanol-stabilized Formaldehyde:

83 g of formalin (36% strength solution in water, stabilized with methanol; 1.00 mol of formaldehyde) are placed in a reaction vessel and 77 g of dimethylamine solution (60% strength solution in water; 1.02 mol of dimethylamine) are added dropwise over a period of 20 minutes (T<35° C.). The solution is cooled to about 20° C., 27 g (1.00 mol) of hydrocyanic acid are added a little at a time (T<35° C.) and the mixture is stirred for another 1 hour at about 20° C. The product solution contains 45% of DMAA in water and can be used further as raw material for syntheses without additional work-up. In the following: ICN=iodine colour number in accordance with DIN 6162; L*ab=colour indices in accordance with DIN 6174.

The values were measured directly after the synthesis and after various storage times in the dark in a closed glass vessel.

| Time of measurement | ICN | L* | a | b |
|---|---|---|---|---|
| immediately after synthesis | 0.2 | 100.1 | −0.7 | 1.7 |
| storage in the dark for 4 days | 0.3 | 100.3 | −1.1 | 2.6 |
| storage in the dark for 10 days | 0.5 | 100.0 | −1.7 | 4.4 |
| storage in the dark for 30 days | 1.4 | 98.7 | −3.2 | 8.7 |

Comparative Example 2

Preparation of an Aqueous DMAA Solution from Paraformaldehyde: 77 g of dimethylamine solution (60% strength solution in water; 1.02 mol of dimethylamine) are placed in a reaction vessel and 31 g of paraformaldehyde are added a little at a time (T<35° C.). The solution is cooled to about 20° C. and 27 g (1.00 mol) of hydrocyanic acid are added a little at a time (T<35° C.). The solution is heated at about 40° C. for 5 minutes in order to dissolve the paraformaldehyde completely and is then stirred for another 1 hour at about 20° C. The product solution contains 63% of DMAA in water and can be used further as raw material for syntheses without additional work-up.

| Time of measurement | ICN | L* | a | b |
|---|---|---|---|---|
| immediately after synthesis | 0.1 | 100.1 | −0.3 | 0.9 |
| storage in the dark for 4 days | 0.1 | 100.2 | −0.5 | 1.4 |
| storage in the dark for 10 days | 0.4 | 99.9 | −1.1 | 3.1 |
| storage in the dark for 30 days | 1.1 | 99.7 | −3.2 | 8.1 |

Comparative Example 3

Preparation of an Aqueous DMAA Solution Purified by Distillation:

The product solution from Comparative Example 1 is fractionally distilled at atmospheric pressure. 49% strength DMAA is obtained from the azeotropic distillation.

| Time of measurement | ICN | L* | a | b |
|---|---|---|---|---|
| immediately after distillation | 0.0 | 100.1 | −0.3 | 0.9 |
| storage in the dark for 4 days | 0.0 | 100.5 | −0.2 | 0.5 |
| storage in the dark for 10 days | 0.0 | 100.3 | −0.3 | 0.7 |
| storage in the dark for 30 days | 0.3 | 100.1 | −1.0 | 2.4 |

Example 4

Preparation of an Aqueous DMAA Solution from 2,4-Diamino-6-phenyl-1,3,5-triazine(benzoguanamine)-stabilized Formaldehyde: 81 g of formalin [37% strength solution in water, stabilized with 840 ppm of 2,4-diamino-6-phenyl-1,3,5-triazine; 1.00 mol of formaldehyde] are placed in a reaction vessel and 77 g of dimethylamine solution (60% strength solution in water; 1.02 mol of dimethylamine) are added dropwise over a period of 20 minutes (T<35° C.). The solution is cooled to about 20° C., 27 g (1.00 mol) of hydrocyanic acid are added a little at a time (T<35° C.) and the mixture is stirred for another 1 hour at about 200° C. The product solution contains 45% of DMAA in water and can be used further as raw material for syntheses without additional work-up.

| Time of measurement | ICN | L* | a | b |
|---|---|---|---|---|
| immediately after synthesis | 0.0 | 100.3 | −0.1 | 0.2 |
| storage in the dark for 4 days | 0.0 | 100.4 | −0.2 | 0.5 |
| storage in the dark for 10 days | 0.3 | 99.4 | −0.5 | 1.2 |
| storage in the dark for 30 days | 0.6 | 99.8 | −1.7 | 4.4 |

Table: Change in the colour over time 5 ml of an aqueous DMAA solution are stored in the dark in a closed glass vessel.

| Solution from Example: | ICN immediately after synthesis | ICN after 4 days | ICN after 10 days | ICN after 30 days |
|---|---|---|---|---|
| No. 1 | 0.2 | 0.3 | 0.5 | 1.4 |
| No. 2 | 0.1 | 0.1 | 0.4 | 1.1 |
| No. 3 | 0.0 | 0.0 | 0.0 | 0.3 |
| No. 4 | 0.0 | 0.0 | 0.3 | 0.6 |

The measurements clearly show the excellent colour stability of the DMMA solution prepared according to the invention, which is virtually as good as that of a solution which has additionally been purified by distillation.

What is claimed is:

1. Process for preparing a colour-stable, aqueous dimethylaminoacetonitrile solution from a formaldehyde source, dimethylamine and hydrocyanic acid, wherein the reaction mixture contains 2,4-diamino-6-phenyl-1,3,5-triazine(benzoguanamine) in a concentration of from 0.001 to 5% by weight, based on formaldehyde, prior to the reaction and the starting substances are used stoichiometrically or in a ratio of 0.98–1.02 mol of formaldehyde and 0.95–1.10 mol of dimethylamine per mol of hydrocyanic acid.

2. Process according to claim 1, wherein the concentration of 2,4-diamino-6-phenyl-1,3,5-triazine is from 0.05 to 0.7% by weight.

3. Process according to claim 1, wherein the starting materials react with one another over a period of from 5 minutes to 5 hours.

4. Process according to claim 1, wherein the starting materials are combined in a continuously operated production process.

5. Process according to claim 1, wherein the reaction temperature is from 0 to 50° C.

6. Process according to claim 1, wherein the reaction temperature is from 25 to 35° C.

7. Process according to claim 1, wherein the formaldehyde source is an aqueous formaldehyde solution (formalin).

8. Process according to claim 1, wherein the formaldehyde source is paraformaldehyde.

9. Process according to claim 1, wherein the concentration of dimethylamine in the aqueous dimethylamine starting solution is from 20 to 80% by weight.

10. Process according to claim 1, wherein the concentration of dimethylamine in the aqueous dimethylamine starting solution is from 35 to 65% by weight.

11. Aqueous dimethylaminoacetonitrile solution containing 2,4-diamino-6-phenyl-1,3,5-triazine in a concentration of from 0.001 to 2.0% by weight, based on the dimethylaminoacetonitrile.

12. Aqueous dimethylaminoacetonitrile solution containing 2,4-diamino-6-phenyl-1,3,5-triazine in a concentration of from 0.01 to 0.25% by weight, based on the dimethylaminoacetonitrile.

13. A colour-stable aqueous dimethylaminoacetonitrile solution comprising 2,4-diamino-6-phenyl-1,3,5-triazine.

14. The colour-stable aqueous dimethylaminoacetonitrile solution according to claim 13, wherein the concentration of the 2,4-diamino-6-phenyl-1,3,5-triazine in the aqueous dimethylaminoacetonitrile solution is from 0.001 to 2.0% by weight, based on the aqueous dimethylaminoacetonitrile solution.

15. The colour-stable aqueous dimethylaminoacetonitrile solution according to claim 13, wherein the concentration of the 2,4-diamino-6-phenyl-1,3,5-triazine in the aqueous dimethylaminoacetonitrile solution is from 0.01 to 0.25% by weight, based on the aqueous dimethylaminoacetonitrile solution.

* * * * *